United States Patent [19]

Fünfschilling

[11] 4,079,065
[45] Mar. 14, 1978

[54] PROCESS FOR THE PRODUCTION OF 2H-CYCLOPENTA (b) FURAN-2-ONE COMPOUNDS

[75] Inventor: Peter Fünfschilling, Basel, Switzerland

[73] Assignee: Sandoz Ltd., Basel, Switzerland

[21] Appl. No.: 765,560

[22] Filed: Feb. 4, 1977

[30] Foreign Application Priority Data

Feb. 11, 1976 Switzerland ................. 1650/70

[51] Int. Cl.² ........................................ C07D 307/77
[52] U.S. Cl. .................... 260/343.3 P; 260/343.41; 260/586 F; 260/586 G; 260/590 B; 260/611 A; 260/617 F
[58] Field of Search ............... 260/343.3 P, 343.2 R, 260/586 F, 586 G, 590 B, 617 F, 611 A, 343.2 F

[56] References Cited

U.S. PATENT DOCUMENTS

| | | | |
|---|---|---|---|
| 3,862,178 | 1/1974 | Brown | 260/586 G |
| 3,872,107 | 3/1975 | Crabbe | 260/586 G |
| 3,892,733 | 7/1975 | Brown | 260/343.3 P |
| 3,943,151 | 3/1976 | Corey | 260/617 F |
| 3,952,019 | 4/1976 | Peel | 260/343.3 P |
| 4,020,172 | 4/1977 | Peel | 260/343.2 R |

*Primary Examiner*—Natalie Trousof
*Assistant Examiner*—Jane T. Fan
*Attorney, Agent, or Firm*—Gerald D. Sharkin; Robert S. Honor; Timothy G. Rothwell

[57] ABSTRACT

The present invention concerns a novel process for preparing derivatives useful in the production of prostaglandins.

The present invention provides a process for the production of a compound of formula I

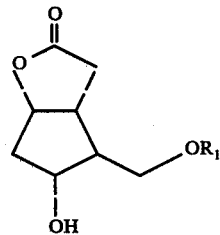

wherein $R_1$ is a protecting group which comprises hydrolyzing a compound of formula II

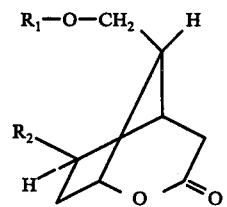

wherein $R_1$ is as defined above and
$R_2$ is a leaving group, under acidic conditions.

8 Claims, No Drawings

PROCESS FOR THE PRODUCTION OF 2H-CYCLOPENTA (b) FURAN-2-ONE COMPOUNDS

The present invention concerns a novel process for preparing derivatives useful in the production of prostaglandins.

The present invention provides a process for the production of a compound of formula I

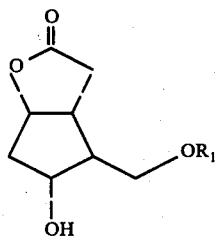

wherein $R_1$ is a protecting group which comprises hydrolysing a compound of formula II

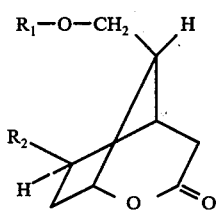

wherein $R_1$ is as defined above and
$R_2$ is a leaving group, under acidic conditions.

The reaction is effected in the presence of an aqueous acid, using conditions such that the group $R_1$ is not split off. The group $R_1$ is thus an acid stable group, but as will be appreciated from the preferred preparation of the compound of formula II as described hereinafter $R_1$ is also preferably a group inert under oxidation conditions, and from the preferred use of the compound of formula I as described hereinafter $R_1$ may also be capable of being selectively split off in the presence of an ester group. A suitable group is benzyl which may be substituted in the phenyl ring with at least one inert substituent.

$R_2$ is a group capable of leaving under aqueous acidic conditions, e.g. acetoxy or preferably chloro or bromo.

The reaction is conveniently effected in the presence of a strong acid, e.g. a strong organic acid, such as p-toluene sulphonic acid, or preferably a mineral acid such as HCl or HBr.

The reaction medium is conveniently more acidic than pH 2. Preferably the pH is from 0.5 to 2, e.g. 1 to 2.

The reaction temperature is conveniently from 0° to 90° C. It is to be appreciated that when high temperatures are used, e.g. from 50° to 90° C, weaker acidic conditions can be tolerated than at low temperatures, e.g. 0° to 20° C, thereby minimising side reactions.

It is preferred to use a inert water-miscible organic solvent such as acetone, tetrahydrofuran or dioxane.

The resultant compound of formula I may be isolated and purified in conventional manner.

A compound of formula II may be obtained in conventional manner by oxidising a compound of formula III

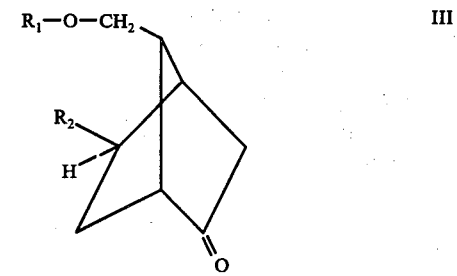

wherein $R_1$ and $R_2$ are defined above e.g. using m-chloroperbenzoic acid.

A compound of formula III may be obtained in conventional manner by reacting a compound of formula IV

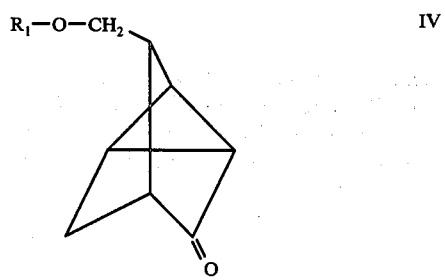

wherein $R_1$ is as defined in claim 1 with a compound of formula $R_2H$ wherein $R_2$ is as defined above.

A compound of formula IV may be obtained by oxidising a compound of formula V

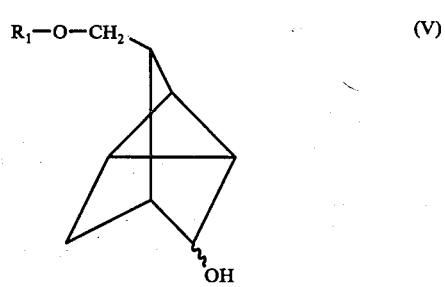

wherein $R_1$ is as defined above in conventional manner, e.g. with chromium trioxide in acetone.

A compound of formula V may be obtained by selectively protecting the hydroxy methyl group in the known compound of formula VI

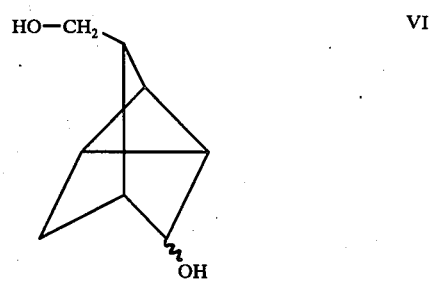

It is to be appreciated that in a compound of formula V or VI the hydroxy group may be in the $\alpha$ or $\beta$ position. Alternatively a compound of formula V or VI may be used as a mixture of the $\alpha$ and $\beta$-isomers.

Insofar as the production of any starting material is not particularly described, this may be produced and purified in analogous manner to known processes or to processes described herein.

As already indicated, the compounds of formula I are known useful intermediates for the production of prostaglandins and intermediates therefor. For example a compound of formula I may be acylated with an acid halide to yield the known compounds of formula VII,

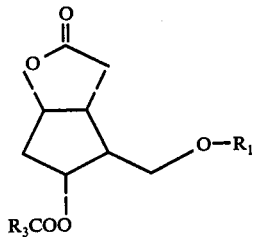

VII wherein $R_1$ is as defined above, e.g. benzyl, and $R_3CO$ is acyl, e.g. $pC_6H_5.C_6H_4.CO$.

The compound of formula VII may be selectively deprotected to produce the known compounds of formula VIII

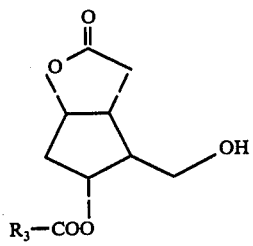

VIII wherein $R_3.CO$ is as defined above.

Processes for the production for the compounds of formulae VII and VIII using a compound of formulae II, III, IV or V are novel and form part of the invention. Compounds of formulae II, III, IV and V are also novel and also form part of the invention.

In the following Examples all temperatures are uncorrected.

EXAMPLE r-4-benzyloxymethyl-3,t-3a,4,5,6,t-6a-hexahydro-t-5-hydroxy-2H-cyclopenta[b]furan-2-one [compound of formula I]

A mixture consisting of 11.5 g of 8-anti-benzyloxymethyl-6-exo-chloro-2-oxabicyclo[3.2.1]octan-3-one, 90 ml of actone, 30 ml of water and 6 ml of 10% hydrochloric acid is heated to reflux for 15 hours. The acetone is removed in a vacuum and 27 ml of 10% caustic soda is added to the residue, a two-phase mixture, and this is stirred for two hours at room temperature. It is then acidified (pH = 2) with 1,5 ml of concentrated hydrochloric acid, and the aqueous phase is extracted in three portions with chloroform. The combined chloroform extracts are washed once with saturated sodium bicarbonate solution, dried over sodium sulphate and evaporated in a vacuum to give the title compound.

The 8-anti-benzyloxymethyl-6-exo-chloro-2-oxabicyclo [3.2.1]octan-3-one used as the starting compound is produced as follows:

(A)
7-anti-benzyloxymethyl-tricyclo[2.2.1.0$^{2,6}$]heptan-3-α and β-ol 8.0 g of a mixture of 3α and 3β-hydroxy-tricyclo [2.2.1.0$^{2,6}$]heptan-7-anti-methanol which has been dissolved in 10 ml of tetrahydrofuran are added in drops in a nitrogen atmosphere at a reaction temperature of 60° C to a suspension of 6.12 g of sodium hydride in 125 ml of toluene. The reaction temperature is then increased to 85° C, and 31.6 g of benzyl chloride, dissolved in 50 ml of toluene, together with 17 g of a mixture of 3α- and 3β-hydroxytricyclo[2.2.1.0$^{2,6}$] heptan-7-anti-methanol, dissolved in 20 ml of tetrahydrofuran, are added simultaneously over the course of 15 minutes. After this addition, the mixture is stirred for another 45 minutes at 85° C, and then 85 ml of 3% ammonium chloride solution are added with cooling by ice. After separating the aqueous phase, the organic phase is washed with 10% tartaric acid solution, dried over sodium sulphate and compressed in a vacuum. The residue, a bright oil, is subjected to distillation. The 7-anti-benzyloxymethyl-tricyclo[2.2.1.0$^{2,6}$]heptan-3α and β-ol mixture is distilled over at a boiling point of 120°–122° C (0.02 mm) as a colourless, slightly viscose oil.

(B) 7-anti-benzyloxymethyl-tricyclo[2.2.1.0$^{2,6}$]heptan 3-one 2.76 g of chormium trioxide and 2.25 ml of concentrated sulphuric acid, dissolved in 10 ml of water, are added in drops with ice cooling over the course of 30 minutes to a solution of 9.6 g of 7-anti-benzyloxymethyl-tricyclo[2.2.1.0$^{2,6}$]heptan-3α and β-ol mixture in 150 ml of actone. This is subsequently stirred for 30 minutes, the actone is removed in a vacuum, and the concentrate is extracted with toluene in two portions. The toluene phase is washed with saturated sodium bicarbonate solution, dried over sodium sulphate and compressed in a vacuum until dry. The yellow oil which is produced in purified by chromatography on silica gel and the pure 7-anti-benzyloxymethyl-tricyclo [2.2.1.0$^{2,6}$]heptan-3-one is thus obtained.

(C)
7-anti-benzyloxymethyl-5-exo-chlorobicyclo[2.2.1]heptan-3-one 50 g of 7-anti-benzyloxymethyl-tricyclo[2.2.1.0$^{2,6}$]-heptan-3-one are dissolved with ice cooling in 750 ml of ethanolic hydrochloric acid (33% g/g) and are stirred for 4.5 hours at an internal temperature of 4° C. 150 ml of water are added in drops over the course of 15 minutes, whereby the temperature increases to 20° C. The reaction mixture is then concentrated in a vacuum and the evaporation residue is absorbed in 400 ml of water and 500 ml of toluene. After vigorous shaking, the aqueous phase is separated and the organic phase is washed successively with 300 ml of water, 300 ml of saturated sodium bicarbonate solution and 600 ml of water. After drying over sodium sulphate, the toluene phase is concentrated in a vacuum and the residue, a slightly yellow oil, is subjected to distillation. The 7-anti-benzyloxymethyl-5-exo-chloro-bicyclo[2.2.1]heptan-3-one is distilled over at a boiling point of 145°–146° C (0.02 mm).

(D)

8-anti-benzyloxymethyl-6-exo-chloro-2-oxabicy-clo[3.2.1]octan-3-one

A solution of 53.6 g of m-chloroperbenzoic acid in 530 ml of methylene chloride is added in drops over the course of one hour at 20°–22° C (water bath cooling) to a mixture consisting of 56.0 g of anti-benzyloxymethyl-5-exo-chlorobicyclo[2.2.1]heptan-3-one, 23.3 g of sodium bicarbonate and 850 ml of methylene chloride. The reaction mixture is subsequently stirred at room temperature for four hours. It is then cooled by an ice bath and after stirring for half an hour, it is filtered. 200 ml of 7% caustic soda are added to the filtrate with ice cooling. The organic phase is separated and is washed successively with 400 ml of water, 300 ml of 10% sodium bisulphite solution, 200 ml of saturated sodium bicarbonate solution and finally 400ml of water. The methylene chloride phase thus treated is dried over sodium sulphate and completely concentrated in a vacuum. This produces a bright yellow oil, consisting of 8-anti-benzyloxy-methyl-6-exo-chloro-2-oxabicyclo[3.2.1.]octan-3-one.

I claim:

1. A process for the production of a compound of formula I

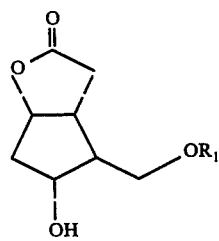

wherein $R_1$ is a protecting group which comprises hydrolysing a compound of formula II

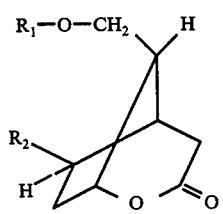

wherein $R_1$ is as defined above, and $R_2$ is a leaving group under acidic conditions at a pH which is more acidic than $pH_2$.

2. A process according to claim 1 effected at a pH of from 0.5 to 2.

3. A process according to claim 1, wherein the compound of formula II is obtained by oxidising a compound of formula III,

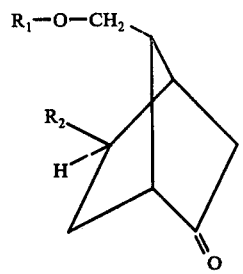

wherein $R_1$ and $R_2$ are as defined in claim 1.

4. A process according to claim 3 wherein the compound of formula III is obtained by reacting a compound of formula IV

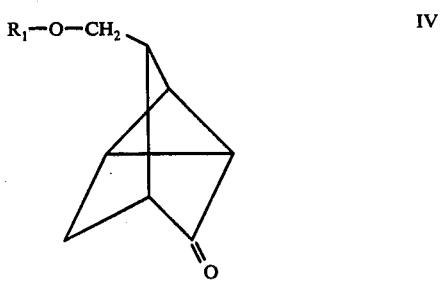

wherein $R_1$ is as defined in claim 4, with a compound $HR_2$ wherein $R_2$ is as defined in claim 1.

5. A process according to claim 1 wherein $R_2$ is chlorine or bromine.

6. A process according to claim 4, wherein the compound of formula IV is obtained by oxidising a compound of formula V

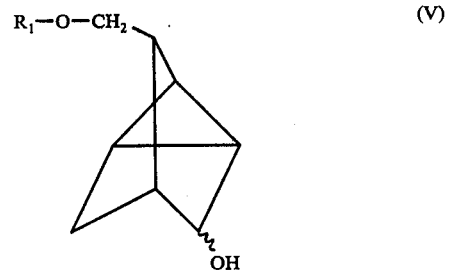

wherein $R_1$ is as defined in claim 5.

7. A process according to claim 1 wherein $R_1$ is benzyl.

8. A process according to claim 6, wherein a compound of formula V is obtained selectively protecting the hydroxymethyl group in a compound of formula VI,

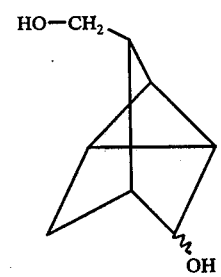

* * * * *